US009808217B2

(12) United States Patent
Homma et al.

(10) Patent No.: US 9,808,217 B2
(45) Date of Patent: Nov. 7, 2017

(54) BREAST CANCER DETECTION SYSTEM, BREAST CANCER DETECTION METHOD, BREAST CANCER DETECTION PROGRAM, AND COMPUTER-READABLE RECORDING MEDIUM HAVING BREAST CANCER DETECTION PROGRAM RECORDED THEREON (71) Applicant: TOHOKU UNIVERSITY, Sendai-shi, Miyagi (JP)

(72) Inventors: Noriyasu Homma, Sendai (JP); Takeshi Handa, Sendai (JP); Tadashi Ishibashi, Sendai (JP); Yusuke Kawasumi, Sendai (JP); Makoto Yoshizawa, Sendai (JP)

(73) Assignee: TOHOKU UNIVERSITY, Sendai (JP)

( * ) Notice: Subject to any disclaimer, the term of this patent is extended or adjusted under 35 U.S.C. 154(b) by 86 days.

(21) Appl. No.: 14/892,134

(22) PCT Filed: Nov. 29, 2013

(86) PCT No.: PCT/JP2013/082126
§ 371 (c)(1),
(2) Date: Nov. 18, 2015

(87) PCT Pub. No.: WO2014/192187
PCT Pub. Date: Dec. 4, 2014

(65) Prior Publication Data
US 2016/0106388 A1      Apr. 21, 2016

(30) Foreign Application Priority Data

May 31, 2013    (JP) .................................. 2013-115007

(51) Int. Cl.
*G06T 7/00*        (2017.01)
*A61B 6/00*        (2006.01)
(Continued)

(52) U.S. Cl.
CPC ............ *A61B 6/5217* (2013.01); *A61B 6/502* (2013.01); *G06K 9/00503* (2013.01);
(Continued)

(58) Field of Classification Search
CPC ....... G06T 7/0012; G06T 7/0014; G06T 7/40; G06T 7/49; G06T 2207/30068; G06T 2207/30096; A61B 6/502; A61B 6/5217
See application file for complete search history.

(56) References Cited

FOREIGN PATENT DOCUMENTS

JP      2004-209059 A      7/2004
JP      2004-313478 A      11/2004
(Continued)

OTHER PUBLICATIONS

Sampat, M.P. et al. "Evidence Based Detection of Spiculated Masses and Architectural Distortions". Proc of SPIE, 2005, vol. 5747, p. 26-37.
Rangayyan, R. M. and F. J. Ayres. "Gabor Filters and Phase Portraits for the Detection of Architectural Distortion in Mammograms". Medical and Biological Engineering and Computing, 2006, 44(10), p. 883-894.
(Continued)

*Primary Examiner* — Andrew W Johns
(74) *Attorney, Agent, or Firm* — Oliff PLC (57) ABSTRACT A model calculating device calculates a mammary gland normal architecture model that scatters in a fan shape from the nipple toward the greater pectoral muscle with respect to the X-ray image of the breast. An orientation extracting device extracts linear components orientations of a region image texture that form a shape of a shadow in the breast X-ray image using a Gabor filter. A lesion determining device compares the mammary gland orientation in the normal architecture model calculated by the model calculating device and the orientation extracted by the orientation extracting device with respect to a region of interest in the X-ray image of the breast including architectural distortion candidates of the mammary gland detected by a preprocessing device to calculate a feature quantity based on a differ-
(Continued)

ence between the orientations and determines whether the candidates are an architectural distortion of the mammary gland based on the feature quantity.

17 Claims, 5 Drawing Sheets

(51) Int. Cl.
    *G06K 9/00*         (2006.01)
    *G06K 9/46*         (2006.01)
    *G06K 9/62*         (2006.01)

(52) U.S. Cl.
    CPC ......... *G06K 9/4609* (2013.01); *G06K 9/4619* (2013.01); *G06K 9/6201* (2013.01); *G06T 7/0012* (2013.01); *G06K 2009/6213* (2013.01); *G06T 2207/10116* (2013.01); *G06T 2207/20076* (2013.01); *G06T 2207/30068* (2013.01); *G06T 2207/30096* (2013.01)

(56) References Cited

FOREIGN PATENT DOCUMENTS

| | | |
|---|---|---|
| JP | 2008-086400 A | 4/2008 |
| JP | 2008-284285 A | 11/2008 |
| JP | 2009-512511 A | 3/2009 |
| WO | 2007/050340 A1 | 5/2007 |

OTHER PUBLICATIONS

Handa, T. et al. "DoG-Based Detection of Architectural Distortion in Mammographic Images for Computer-Aided Detection". SICE Annual Conference, 2012, p. 762-767.

Ichikawa, Tetsuko et al. "Automated Detection Method for Architectural Distortion Areas on Mammograms Based on Morphological Processing and Surface Analysis". Medical Imaging 2004, Proc of SPIE, May 2004, vol. 5370, p. 920-925.

Minavathi et al. "Model Based Approach for Detection of Architectural Distortions and Spiculated Masses in Mammograms". International Journal on Computer Science and Engineering, Nov. 2011, vol. 3 No. 11, p. 3534-3546.

Ayres, F. J et al. "Characterization of Architectural Distortion in Mammograms". IEEE Engineering in Medicine and Biology Magazine, Jan. 2005, vol. 24, No. 1, p. 59-67.

Zhou, Xiangrong et al. "Anatomical Structure Recognition of Normal Torso Region in Non-Contrast CT Images". Medical Imaging Technology, May 2006, vol. 24, No. 3, pp. 167-172.

Honma, Noriyasu. "Development of Computer-Aided Diagnosis Systems for Detection of Architectural Distortion in Mammograms". Bulletin of School of Health Sciences Tohoku University, Jul. 31, 2013, vol. 22, No. 2, pp. 67-77.

Rangayyan, Rangaraj M. "Computer-Aided Detection of Subtle Signs of Early Breast Cancer: Detection of Architectural Distortion in Mammograms". Department of Electrical and Computer Engineering, University of Calgary, May 31, 2013.

Feb. 10, 2014 International Search Report issued in International Patent Application No. PCT/JP2013/082126.

BREAST CANCER DETECTION SYSTEM, BREAST CANCER DETECTION METHOD, BREAST CANCER DETECTION PROGRAM, AND COMPUTER-READABLE RECORDING MEDIUM HAVING BREAST CANCER DETECTION PROGRAM RECORDED THEREON

TECHNICAL FIELD

The present invention relates to a breast cancer detection system, a breast cancer detection method, a breast cancer detection program, and a computer-readable recording medium having the breast cancer detection program recorded thereon.

BACKGROUND ART

In general, a dramatic improvement in the survival rate of the cancer can be expected by early detection and treatment. In recent years, mammographic X-ray radiography (mammography) is often used as effective means for early detection of breast cancer. Mammography can examine the state of the entire breast and can effectively detect very small lesions which are hard to detect by visual and palpation-based examinations and in ultrasound images.

However, when the number of patients examined by mammography increases, the physician's load increases, which can cause misdiagnosis or overlooking of lesions due to fatigue or the like. Thus, in order to reduce the medical examiner's load and improve the diagnosis accuracy, a computer-aided detection or diagnosis (CAD) system has been developed. CAD is a technique for improving the quality and productivity of diagnosis such as an improvement in diagnosis accuracy and a reduction in the time required for diagnosis by presenting computer-aided image analysis information to a radiologist as a second opinion.

Examples of major imaging findings on breast cancer include microcalcifications, masses, and architectural distortions. Microcalcifications are the dead and deposited cells of blood vessels or soft tissues in the breast and visually recognized as clusters of white specks on an image. Masses are space-occupying lesions having features in their shape, boundary, and density and appear as shadows having a certain extent of area on an image. Architectural distortions are not clear mass shadows but are lesions in which a normal mammary gland architecture involves distortions and have features such as speculations wherein the mammary gland scatters in a radial form from one point and substantial local retractions or distortions of the mammary gland. This architectural distortion is a lesion that is more difficult to interpret and more likely to be overlooked than other findings.

Since these findings on breast cancer have respective specific image features, CAD systems that detect respective specific findings have been developed (for example, see Patent Literature 1). Among these findings, as for architectural distortions that are particularly difficult to interpret, CAD systems based on various approaches have been proposed. For example, a method of calculating a linear concentration and a directional distribution index of a linear component of an image texture of a region to calculate candidates for architectural distortions based on the product of the two values is known (for example, see Patent Literature 2). Moreover, a method of enhancing a linear component of an original image texture of a region by the Radon transform and enhancing a radial linear component associated with the shadows of architectural distortions using a radial filter designed exclusively for the radial linear component to detect the candidates for architectural distortions is known. Further, a method of creating a model by diagnosing an orientation map obtained by Gabor filters as a vector field diagram of a linear dynamic system and quantifying the degree of radial linear components of an image texture of a region of a lesion based on the model to detect the candidates for architectural distortions (for example, see Non-Patent Literature 2).

These conventional CAD systems for detecting architectural distortions employ an approach that focuses on features unique to architectural distortions such as scattering (speculations) of linear components of an image texture of a region to quantify the feature. However, X-ray image of the breasts provide extremely high accuracy in terms of spatial resolution and density re whereas the images are likely to contain noise and linear components associated with lesions often appear as shadows that are dimly visible and have extremely low contrast. Thus, it is difficult to extract linear components with sufficient accuracy for determining whether the linear components are lesions and a true-positive fraction is not high enough. Moreover, even when the linear components of the mammary gland are extracted, it is difficult to accurately quantify the feature of a lesion and a false-positive fraction is high.

Thus, the present inventors have proposed a method of detecting the candidates for architectural distortions by focusing on an average intensity difference between a target area and the surrounding area rather than extracting fine linear components of an image texture of a region of which the extraction accuracy is poor (for example, see Non-Patent Literature 3). This method focuses on a new feature that a contrast is present between the central portion of a lesion and its surrounding portion to detect lesion candidates having the feature by DoG (Difference of Gaussians) filtering. It is confirmed that this method can detect architectural distortion candidates with a higher true-positive fraction and a lower false-positive fraction at the same true-positive fraction than the conventional CAD systems.

A method of improving the contrast of images associated with lesions in which the linear components of an image texture of a region have an extremely low contrast has been proposed (for example, see Patent Literature 3). However, this method is used for facilitating the interpretation by physicians but is not used for CAD systems. Moreover, a CAD system which uses ultrasound or MRI images other than mammography has been developed (for example, see Patent Literature 4). However, since the images have a lower resolution than mammography, such a CAD system is rarely used. Further, the present inventors has developed a CAD system that extracts inclination segment information from the shadows in an X-ray or CT medical tomographic image using Gabor filters in order to diagnose lung cancer or the like, calculates the feature quantities of the shadows from the information, and determine whether the shadows are abnormal shadows (for example, see Patent Literature 5).

CITATION LIST

Patent Literature

Patent Literature 1: Japanese Unexamined Patent Publication No. 2004-313478
Patent Literature 2: Japanese Unexamined Patent Publication No. 2004-209059
Patent Literature 3: Japanese Unexamined Patent Publication No. 2009-512511

Patent Literature 4: Japanese Unexamined Patent Publication No. 2008-86400

Patent Literature 5: Japanese Unexamined Patent Publication No. 2008-284285

Non-Patent Literature 1: M. P. Sampat, G. J. Whitman, M. K. Markey, and A. C. Bovik, "Evidence based detection of spiculated masses and architectural distortions," Proc of SPIE, 2005, Vol. 5747, p. 26-37

Non-Patent Literature 2: R. M. Rangayyan and F. J. Ayres, "Gabor filters and phase portraits for the detection of architectural distortion in mammograms," Medical and Biological Engineering and Computing, 2006, 44(10), p. 883-894

Non-Patent Literature 3: T. Handa, X. Zhang, N. Homma, T. Ishibashi, Y. Kawasumi, M. Abe, N. Sugita and M. Yoshizawa, "DoG-Based Detection of Architectural Distortion in Mammographic Images for Computer-Aided Detection," Proc of SICE Annual Conference, 2012, p. 762-767

SUMMARY OF INVENTION

Technical Problem

The CAD system for detecting architectural distortions disclosed in Non-Patent Literature 3 can detect candidates for architectural distortions of the mammary gland with a higher true-positive fraction than the conventional CAD systems disclosed in Patent Literature 2 and Non-Patent Literatures 1 and 2. However, the CAD system does not take detailed features of normal architectures of the mammary gland into consideration, the features of lesions are not quantitized accurately and the false-positive fraction becomes worse.

The present invention is made, focusing on the foregoing problem and an object of the present invention is to provide a breast cancer detection system capable of reducing the false-positive fraction, a breast cancer detection method, a breast cancer detection program, and a computer-readable recording medium having the breast cancer detection program recorded thereon.

Solution to Problem

In order to attain the object, a breast cancer detection system according to the present invention is a breast cancer detection system for detecting an architectural distortion of the mammary gland included in an X-ray image of the breast, including: a model calculating means that calculates a normal architecture model of the mammary gland that scatters in a fan shape from the nipple toward the greater pectoral muscle with respect to the X-ray image of the breast; an orientation extracting means that extracts orientations of linear components of an image texture of a region that form a shape of a shadow in the X-ray image of the breast; and a lesion determining means that compares the orientation of the mammary gland in the normal architecture model calculated by the model calculating means and the orientation extracted by the orientation extracting means with respect to a region of interest in the X-ray image of the breast including architectural distortion candidates of the mammary gland detected by preprocessing to calculate a feature quantity based on a difference between the orientations and determines whether the candidates are an architectural distortion of the mammary gland based on the feature quantity.

A breast cancer detection method according to the present invention is a breast cancer detection method for detecting an architectural distortion of the mammary gland included in an X-ray image of the breast, including: a model calculating step of allowing a computer to calculate a normal architecture model of the mammary gland that scatters in a fan shape from the nipple toward the greater pectoral muscle with respect to the X-ray image of the breast; an orientation extracting step of allowing the computer to extract an orientation of linear components of an image texture of a region that form a shape of a shadow in the X-ray image of the breast; and a lesion determining step of allowing the computer to compare the orientation of the mammary gland in the normal architecture model calculated by the model calculating step and the orientation extracted by the orientation extracting step with respect to a region of interest in the X-ray image of the breast including architectural distortion candidates of the mammary gland detected by preprocessing to calculate a feature quantity based on a difference between the orientations and determine whether the candidates are an architectural distortion of the mammary gland based on the feature quantity.

A breast cancer detection program according to the present invention is a breast cancer detection program for detecting an architectural distortion of the mammary gland included in an X-ray image of the breast, the program causing a computer to function as: a model calculating means that calculates a normal architecture model of the mammary gland that scatters in a fan shape from the nipple toward the greater pectoral muscle with respect to the X-ray image of the breast; an orientation extracting means that extracts orientations of linear components of an image texture of a region that form a shape of a shadow in the X-ray image of the breast; and a lesion determining means that compares the orientation of the mammary gland in the normal architecture model calculated by the model calculating means and the orientation extracted by the orientation extracting means with respect to a region of interest in the X-ray image of the breast including architectural distortion candidates of the mammary gland detected by preprocessing to calculate a feature quantity based on a difference between the orientations and determines whether the candidates are an architectural distortion of the mammary gland based on the feature quantity.

A computer-readable recording medium having the breast cancer detection program recorded thereon according to the present invention is a computer-readable recording medium having a breast cancer detection program thereon, for detecting an architectural distortion of the mammary gland included in an X-ray image of the breast, the program causing a computer to function as: a model calculating means that calculates a normal architecture model of the mammary gland that scatters in a fan shape from the nipple toward the greater pectoral muscle with respect to the X-ray image of the breast; an orientation extracting means that extracts orientations of linear components of an image texture of a region that form a shape of a shadow in the X-ray image of the breast; and a lesion determining means that compares the orientation of the mammary gland in the normal architecture model calculated by the model calculating means and the orientation extracted by the orientation extracting means with respect to a region of interest in the X-ray image of the breast including architectural distortion candidates of the mammary gland detected by preprocessing to calculate a feature quantity based on a difference between the orientations and determines whether the candidates are an architectural distortion of the mammary gland based on the feature quantity.

The breast cancer detection system according to the embodiment of the present invention calculates a normal architecture model of the mammary gland, calculates a feature quantity of architectural distortion candidates in an X-ray image of the breast based on the normal architecture model, and determines whether the architectural distortion candidates are architectural distortions based on the feature quantity. Thus, it is possible to accurately quantify the features of lesions by taking the positions of architectural distortion candidates on the breast region into consideration and to make determination. Since the feature quantity is based on the difference between the orientation of the mammary gland in the normal architecture model and the orientation of the linear components that form the shape of the shadows in the X-ray image of the breast, the feature of architectural distortions such as speculations wherein the mammary gland scatters in a radial form from one point can be quantified with high accuracy. In this manner, the breast cancer detection system according to the embodiment of the present invention can reduce a false-positive fraction and accurately detect architectural distortions of the mammary gland as compared to a case where the normal mammary gland architecture is not taken into consideration.

In the breast cancer detection system according to the present invention, the preprocessing for detecting architectural distortion candidates of the mammary gland is preferably realized by a processing system such as the CAD system disclosed in Non-Patent Literature 3, capable of detecting many lesion candidates with a high true-positive fraction. Moreover, the preprocessing may be realized by the conventional CAD systems of Patent Literature 2 or Non-Patent Literature 1 or 2. The breast cancer detection system according to the present invention can divide an entire X-ray image of the breast into a plurality of regions of interest without performing the preprocessing and detect architectural distortions in each region of interest.

In the breast cancer detection system, the breast cancer detection program, and the computer-readable recording medium having the breast cancer detection program recorded thereon according to the present invention, the lesion determining means may calculate the feature quantity R according to the following equation in which, for a plurality of coordinates (x,y) in the region of interest, $\Phi(x,y)$ is the orientation of the mammary gland in the normal architecture model calculated by the model calculating means, $\Theta(x,y)$ is the orientation extracted by the orientation extracting means, $N_m$ is a parameter for determining an allowable range of matching orientations, and $N_{ROI}$ is the number of coordinates.

[Equation 3]

$$R = \frac{\sum_x \sum_y h(x, y)}{N_{ROI}} \quad (1)$$

where $$h(x, y) = \begin{cases} 0, & |\Phi(x, y) - \Theta(x, y)| \leq \frac{\pi}{N_m} \\ 1, & \text{otherwise} \end{cases}$$

In the breast cancer detection method according to the present invention, the lesion determining step may calculate the feature quantity R according to Equation (1) in which, for a plurality of coordinates (x,y) in the region of interest, $\Phi(x,y)$ is the orientation of the mammary gland in the normal architecture model calculated by the model calculating step, $\Theta(x,y)$ is the orientation extracted by the orientation extracting step, $N_m$ is a parameter for determining an allowable range of matching orientations, and $N_{ROI}$ is the number of coordinates.

When Equation (1) is used, when the sum of the differences between the orientation $\Phi(x,y)$ of the mammary gland in the normal architecture model within the region of interest and the orientation $\Theta(x,y)$ of the linear components of the image texture of a region increases, the feature quantity R also increases, and the features of the architectural distortions can be identified accurately. By adjusting the value of the parameter $N_m$ in Equation (1) according to the size, the contrast, and the like of noise in the X-ray image of the breast, it is possible to secure optimal detection accuracy. Moreover, it is possible to adjust a true-positive fraction and a false-positive fraction according to the value of the threshold of the feature quantity R used when determining architectural distortions. The coordinate (x,y) is preferably made up of all pixels in the region of interest in order to make objective determination.

In the breast cancer detection system, the breast cancer detection method, the breast cancer detection program, and the computer-readable recording medium having the breast cancer detection program recorded thereon, a Gabor filter is preferably used for extracting an orientation of linear components in the X-ray image of the breast. In this case, the orientation (inclination segment information) of the linear components that form the shape of the shadow can be extracted efficiently and effectively. The means for extracting the orientation of the linear components may use other known filters such as a curvature detection filter or an edge filter in addition to the method using the Gabor filter. Moreover, Radon transform or thinning processing also may be performed as the method other than the filter processing.

In the breast cancer detection system, the breast cancer detection method, the breast cancer detection program, and the computer-readable recording medium having the breast cancer detection program recorded thereon, the calculated normal architecture model of the mammary gland may be an optional model as long as the mammary gland scatters in a fan shape from the nipple toward the greater pectoral muscle. However, a simple model is preferable from the viewpoint of the easiness of mathematical handling, a calculation amount, or the like. For example, the normal architecture model of the mammary gland that scatters in a fan shape from the nipple toward the greater pectoral muscle may be calculated using an exponential curve, a logarithmic curve, or a parabolic curve of a quadric function.

In the breast cancer detection system, the breast cancer detection method, the breast cancer detection program, and the computer-readable recording medium having the breast cancer detection program recorded thereon, the quantitative value used as the feature quantity preferably represents the difference between the orientation of the mammary gland in the normal architecture model and the orientation of the linear components that form the shape of the shadow in the X-ray image of the breast like the feature quantity R. As another form of the quantitative value, the function h of the feature quantity R may be replaced with a multi-valued function having three or more values, and multi-values histogram information having three or more values may be used for $N_{ROI}$.

Advantageous Effects of Invention

According to the present invention, it is possible to provide a breast cancer detection system capable of reducing a false-positive fraction, a breast cancer detection method, a breast cancer detection program, and a computer-readable recording medium having the breast cancer detection program recorded thereon.

BRIEF DESCRIPTION OF EMBODIMENTS

DESCRIPTION OF EMBODIMENTS

Hereinafter, an embodiment of the present invention will be described with reference to the drawings.

FIGS. 1 to 6 illustrate a breast cancer detection system, a breast cancer detection method, a breast cancer detection program, and a computer-readable recording medium having the breast cancer detection program recorded thereon according to an embodiment of the present invention. The breast cancer detection method according to the embodiment of the present invention is a method which is suitably implemented by the breast cancer detection system according to the embodiment of the present invention and can be executed by a computer with the aid of a computer-readable recording medium such as a hard disk, a DVD-ROM, a CD-ROM, and a flexible disk, having the breast cancer detection program recorded thereon.

Figure 1:
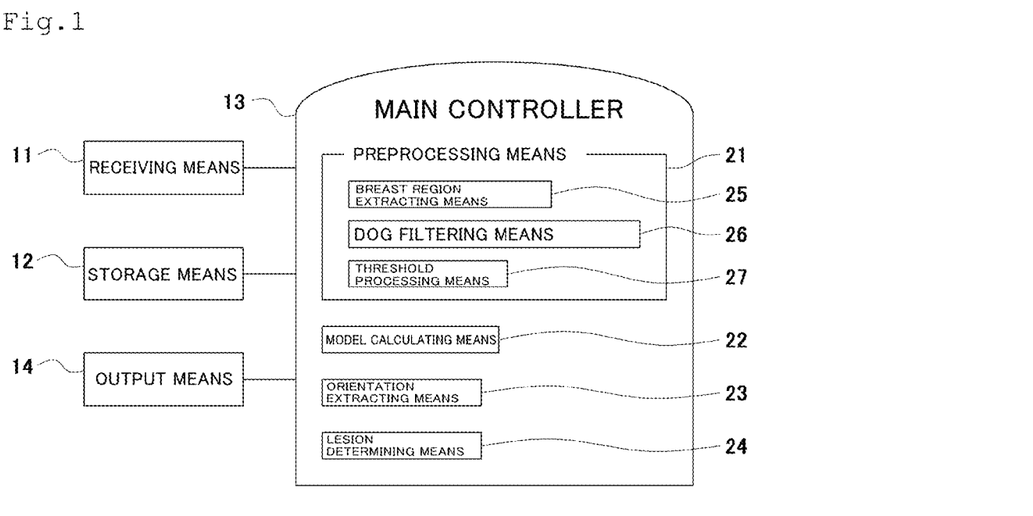
FIG. 1 is a block diagram illustrating a configuration of a breast cancer detection system according to an embodiment of the present invention.

As illustrated in FIG. 1, the breast cancer detection system according to the embodiment of the present invention is a breast cancer detection system for detecting architectural distortions of the mammary gland included in X-ray images of the breast. The breast cancer detection system is implemented as a computer which includes a receiving means 11, a storage means 12 that stores various types of data, a main controller 13 having arithmetic and control functions, and an output means 14.

The receiving means 11 is connected to a mammographic X-ray imaging device (mammography) so as to be able to receive X-ray images of the breast captured by the mammographic X-ray imaging device. The receiving means 11 may be connected to a medical X-ray image server rather than the mammographic X-ray imaging device so as to be able to receive X-ray images of the breast. Moreover, the receiving means 11 may be configured to be able to receive X-ray images of the breast stored in a storage medium such as a CD-R or a DVD-R from the corresponding readers. The storage means 12 is configured with a memory and is configured to store the X-ray images of the breast received from the receiving means 11.

The main controller 13 is implemented as a CPU and is connected to the receiving means 11, the storage means 12, and the output means 14 so as to be able to control the respective components. The main controller 13 includes a preprocessing means 21, a model calculating means 22, an orientation extracting means 23, and a lesion determining means 24.

[Preprocessing Means]

The preprocessing means 21 is configured with the CAD system disclosed in Non-Patent Literature 3, capable of detecting as many lesion candidates as possible with a high true-positive fraction. The preprocessing means 21 includes a breast region extracting means 25, a DoG filtering means 26, and a threshold processing means 27. The breast region extracting means 25 determines the boundary between a pectoral region and a breast region using an image processing method of tracking high edge intensity points and removes a pectoral region in which the mammary gland is not present, from the X-ray image of the breast. Further, the breast region extracting means 25 reduces the image excluding pectoral muscles to the ¼ scale of the original image using a bicubic method in order to reduce the computation time.

The central portion of a shadow of an architectural distortion tends to have a certain extent of contrast in such a way that the luminance intensity is generally higher or lower than that of the peripheral portion. The DoG filtering means 26 performs DoG (Difference of Gaussians) filtering on the X-ray image of the breast to detect a local contrast in order to extract brightness/darkness information associated with such an architectural distortion.

The DoG filtering means 26 detects the local contrast in the following manner. That is, first, the convolution of a 2-dimensional Gaussian kernel G(xG,yG,σ) having a standard deviation σ and an input image I(x,y) is taken to obtain a smoothed image L(x,y,σ) using the following equation.

$$L(x,y,\sigma)=G(xG,yG,\sigma)*I(x,y) \quad (2)$$

Here, xG and yG indicate the distance of the kernel from a target position (x,y), respectively. Moreover, the Gaussian kernel is defined by the following equation.

[Equation 4]

$$G(x_G, y_G, \sigma) = \frac{1}{2\pi\sigma^2}\exp\left(-\frac{x_G^2 + y_G^2}{2\sigma^2}\right) \quad (3)$$

Subsequently, a difference between two images having different smoothing levels is calculated according to Equation (4) to obtain a DoG image $D_k(x,y,\sigma)$.

$$D_k(x,y,\sigma)=L(x,y,k\sigma)-L(x,y,\sigma) \quad (4)$$

k is a parameter that determines the standard deviation (that is, the ratio between smoothing levels) of the 2-dimensional Gaussian kernel. Since the size (area) of a detection target lesion can be controlled by the parameter σ, the DoG filtering means 26 preferably set the parameter σ appropriate for the size of the detection target lesion.

A region having a locally high contrast within the X-ray image of the breast has a high value on an image $D_k$ obtained after the DoG filtering. Thus, The threshold processing means 27 performs threshold processing in order to detect peak values in the image obtained after the DoG filtering. In this case, a threshold is set so as to detect a larger number of peak values while suppressing the area of each region. Moreover, threshold processing is performed on the area of the remaining area in a two-valued image obtained after the threshold processing in order to remove regions having an extremely large or small area. In this way, the preprocessing means 21 extracts the candidates for architectural distortions of the mammary gland.

[Model Calculating Means]

In the case of a normal mammary gland architecture, linear components of an image texture of a region present on a breast region scatter in an approximately fan shape from the nipple to the greater pectoral muscle. The model calculating means 22 calculates a normal architecture model of the mammary gland that scatters in a fan shape from the nipple toward the greater pectoral muscle with respect to a target X-ray image of the breast in order to model the normal mammary gland architecture. First, the model calculating means 22 detects the nipple. In a craniocaudal (CC) image, the greater pectoral muscle is assumed to be vertical and a point farthest from an image end is assumed to be the nipple position. In a mediolateral oblique (MLO) image, a point farthest from a straight line passing through the end points of the greater pectoral muscle is assumed to be the nipple position.

Subsequently, in a coordinate (x,y) illustrated in FIG. 2 when the nipple is at the bottom and the pectoral muscle is on the top, the linear component of a normal mammary gland is approximated by such an exponential curve as the following equation based on the nipple position.

$$y = f(x) = A\exp(Bx) \qquad (5)$$

Here, A and B are parameters of an exponential function, and the coordinate of the nipple serving as the reference is (0, A). On the other hand, among the exponential curves of Equation (5) that passes through the nipple, the parameter $B_i$ of a curve that passes through a certain point $(x_i, y_b)$ on the pectoral muscle side illustrated in FIG. 2 is expressed by the following equation.

$$B_i = B = (1/x_i)\log(y_b/A) \qquad (6)$$

Here, $y_b$ is the y-coordinate when the pectoral muscle is approximated to a straight line.

Figure 2:
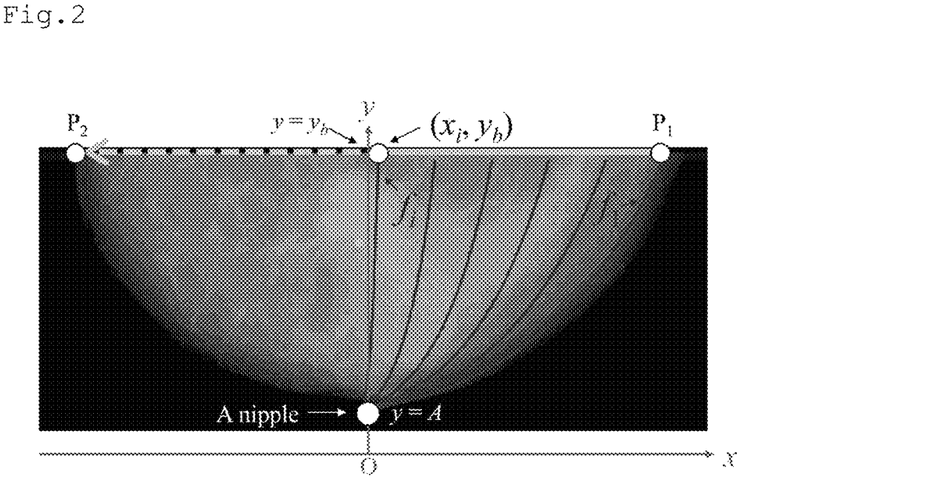
FIG. 2 is an explanatory diagram illustrating a method of calculating a normal architecture model in the breast cancer detection system illustrated in FIG. 1.

If the length of the pectoral muscle (that is, the number of pixels present between points $P_1$ and $P_2$ in FIG. 2) is $N_f$, an exponential curve that passes through the point $(x_i, y_b)$ (i=1, 2, . . . , $N_f$) is expressed by the following equation.

$$y = f_i(x) = A\exp(B_i x) \qquad (7)$$

The model calculating means 22 calculates the normal architecture model of the mammary gland by moving the point $(x_i, y_b)$ from point $P_1$ to point $P_2$ by a step of one pixel to calculate $B_i$ according to Equation (6) and calculate the exponential function $f_i$ according to Equation (7).

Moreover, the model calculating means 22 calculates an angle Φ between the tangent of the exponential function calculated by Equation (7) and the positive direction of the x-axis as the orientation of the mammary gland of the normal architecture model. Φ is given by the following equation.

$$\Phi(x, {}^i y) = \arctan(f'_i(x)) = \arctan(AB_i \exp(B_i x)) \qquad (8)$$

Here, $^i y$ is the y-coordinate that satisfies $y=f_i(x)$. Since Equation (8) cannot be applied to pixels through which the exponential curve does not pass, the pixels are processed by assuming that the pixels through which the exponential curve does not pass have the angle values of pixels which are located closest to the pixels.

[Orientation Extracting Means]

The orientation extracting means 23 extracts the orientation of the linear components that form the shape of the shadow in the X-ray image of the breast using Gabor filters. Gabor filters are used as orientation component feature extraction filters in many image recognition systems such as fingerprint authentication or iris recognition and are widely used in processing medical images such as X-ray images of the breast or computerized tomographic images.

The output g of a Gabor filter is expressed by Equation (9).

[Equation 5]

$$g(x, y) = \exp\left(-\frac{1}{2\sigma_G^2}(x'^2 + \gamma y'^2)\right)\cos\left(2\pi\frac{x'}{\lambda}\right) \qquad (9)$$

where $x' = x\cos\theta + y\sin\theta$ $y' = -x\sin\theta + y\cos\theta$

Here, x and y are coordinates, θ is an angle, σ is a dispersion, γ is an aspect ratio, and λ is a wavelength.

A Gabor filter kernel having an inclination of an i-th angle $\theta_i = \pi i/180$ (i=1, 2, . . . , m) among m discretized angles (m is a natural number) of 180 degrees is defined as $g_i$. In this case, a convolutional integration between $g_i$ and the original image I is expressed by $I_i(x,y) = (I * g_i)(x,y)$, and an orientation map Θ(x,y) of the original image I(x,y) is defined by the following equation.

[Equation 6]

$$\Theta(x, y) = \frac{\pi}{180} i_{max}(x, y) \qquad (10)$$

where $$i_{max}(x, y) = \underset{i}{\operatorname{argmax}}[|I_i(x, y)|]$$

That is, the orientation extracting means 23 calculates the orientation map Θ(x,y) by assuming that an angle $\pi i_{max}/180$ corresponding to i that gives the largest value among m convolutional integration results $|I_i(x,y)|$ is an orientation component of a pixel at the position (x,y).

[Lesion Determining Means]

The lesion determining means 24 compares the orientation Φ(x,y) of the mammary gland in the normal architecture model calculated by the model calculating means 22 and the orientation Θ(x,y) extracted by the orientation extracting means 23 with respect to a region of interest in the X-ray image of the breast including the candidates for architectural distortions of the mammary gland detected by the preprocessing means 21, calculates a feature quantity R based on the difference between the two orientations according to Equation (1), and determines whether the architectural distortion candidates are the architectural distortions of the mammary gland based on the feature quantity R. In calculation of the feature quantity R, h(x,y) is calculated for all coordinates (x,y) in the region of interest. In this case, $N_{ROI}$ is the number of all pixels.

The feature quantity R means that a strict match only is allowed when a parameter $N_m$ that determines an allowable range of the matching orientations has a large value whereas a rough match is also allowed when $N_m$ has a small value. When the orientation map Θ(x,y) matches the orientation Φ(x,y) of the mammary gland in the normal architecture model, the feature quantity R decreases. When architectural distortion shadows are included, since the proportion of the orientation map of which the orientations do not match the orientations of the normal mammary gland increases, the feature quantity R increases. The lesion determining means 24 sets a threshold to the feature quantity R and determines that the architectural distortion candidates are architectural distortions of the mammary gland when the feature quantity R is larger than the threshold.

The main controller 13 transmits the image of the region of interest including the architectural distortion candidates extracted by the preprocessing means 21, the calculation result of the Gabor filter, the calculation result of the feature quantity R, the image of the region of interest determined to be architectural distortions by the lesion determining means 24, and the like to the storage means 12 so that the images and the calculation results are stored in the storage means 12.

The output means 14 is configured with a monitor or a printer. The output means 14 is configured to be able to output the X-ray images of the breast stored in the storage means 12, the image of the region of interest including the architectural distortion candidates extracted by the preprocessing means 21, the calculation result of the Gabor filter, the calculation result of the feature quantity R, the image of the region of interest determined to be architectural distortions by the lesion determining means 24, and the like to a monitor or a printer.

Figure 3:
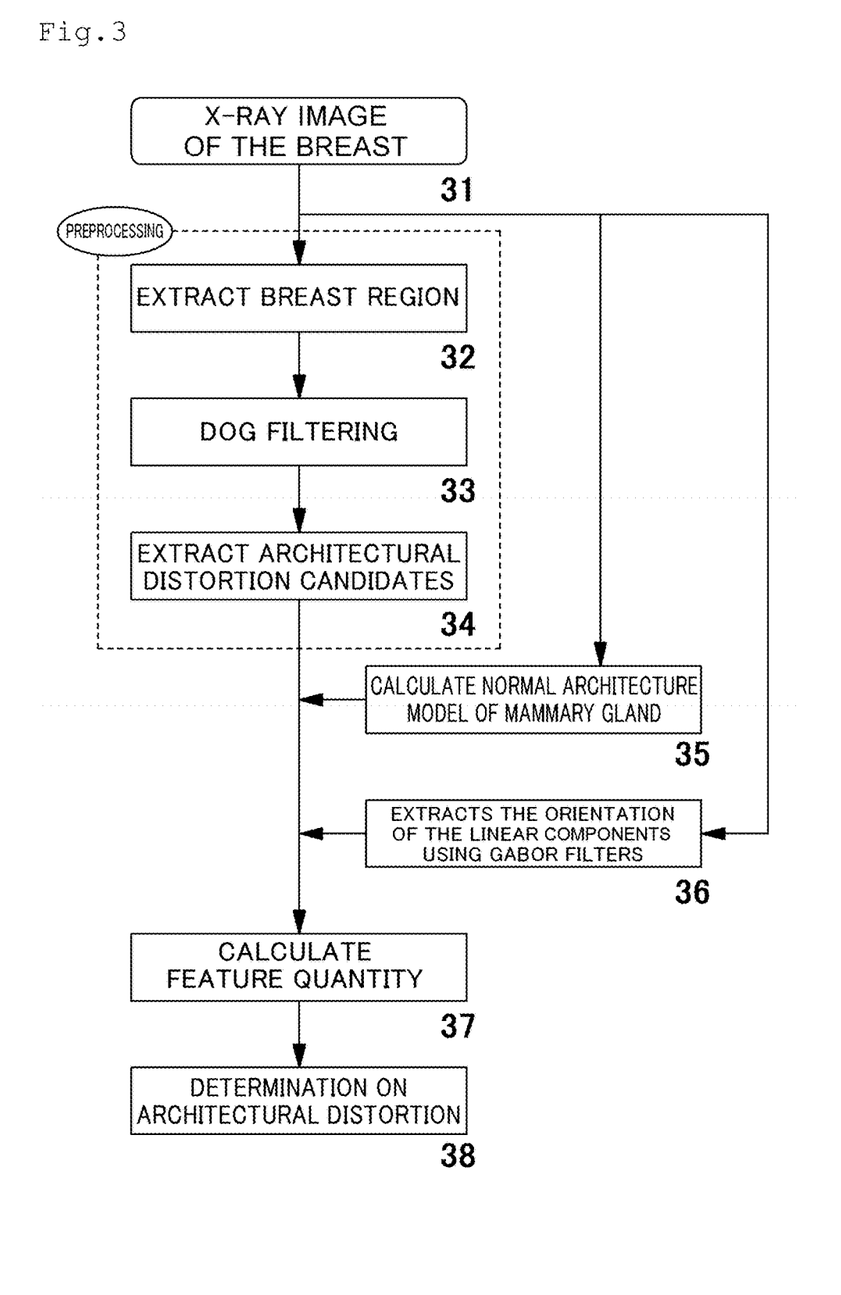
FIG. 3 is a flowchart illustrating the flow of processes of the breast cancer detection system illustrated in FIG. 1.
Figure 4:
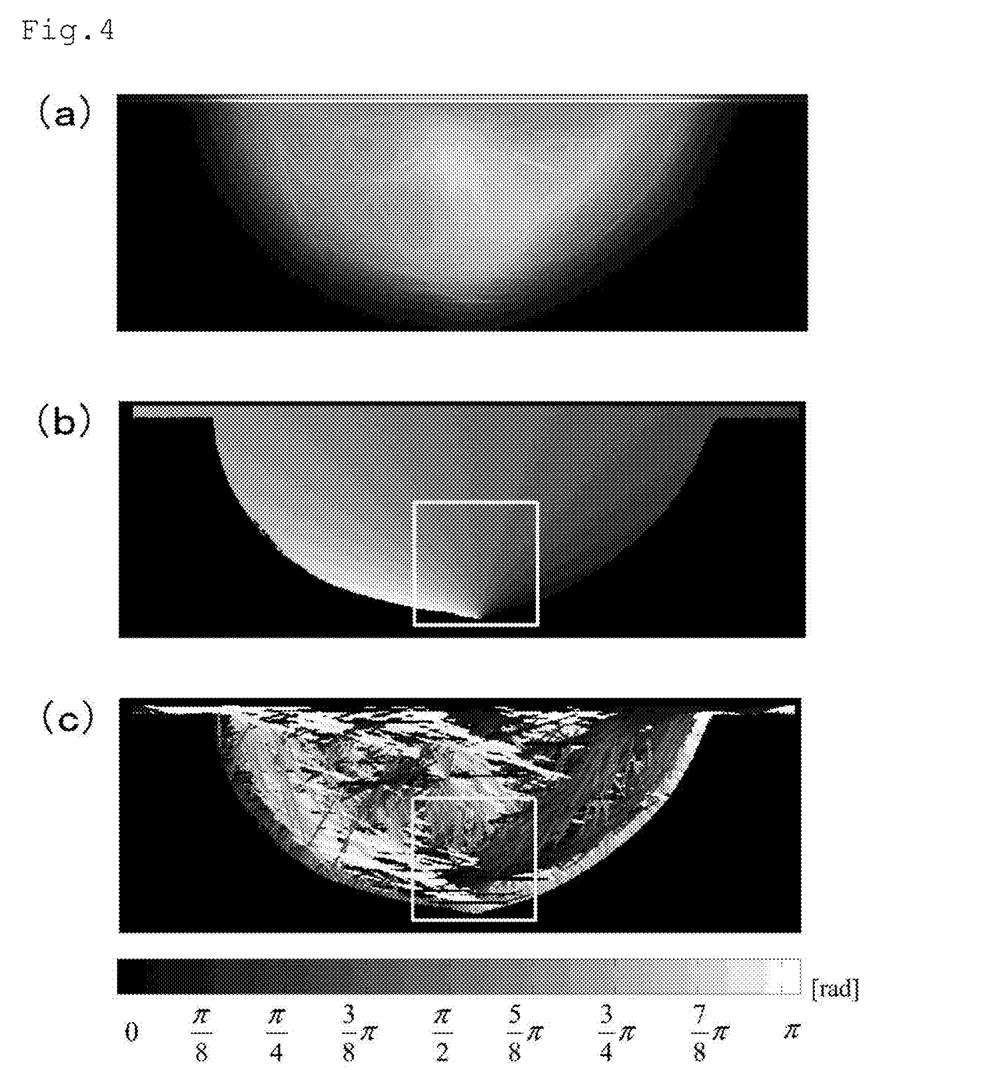
FIG. 4(a) illustrates an X-ray image of the breast received by the breast cancer detection system illustrated in FIG. 1.
FIG. 4(b) illustrates an orientation Φ of the mammary gland in a normal architecture model obtained for the X-ray image of the breast in FIG. 4(a)
FIG. 4(c) illustrates an image illustrating an orientation Θ of linear components extracted from the X-ray image of the breast in FIG. 4(a).
Figure 5:
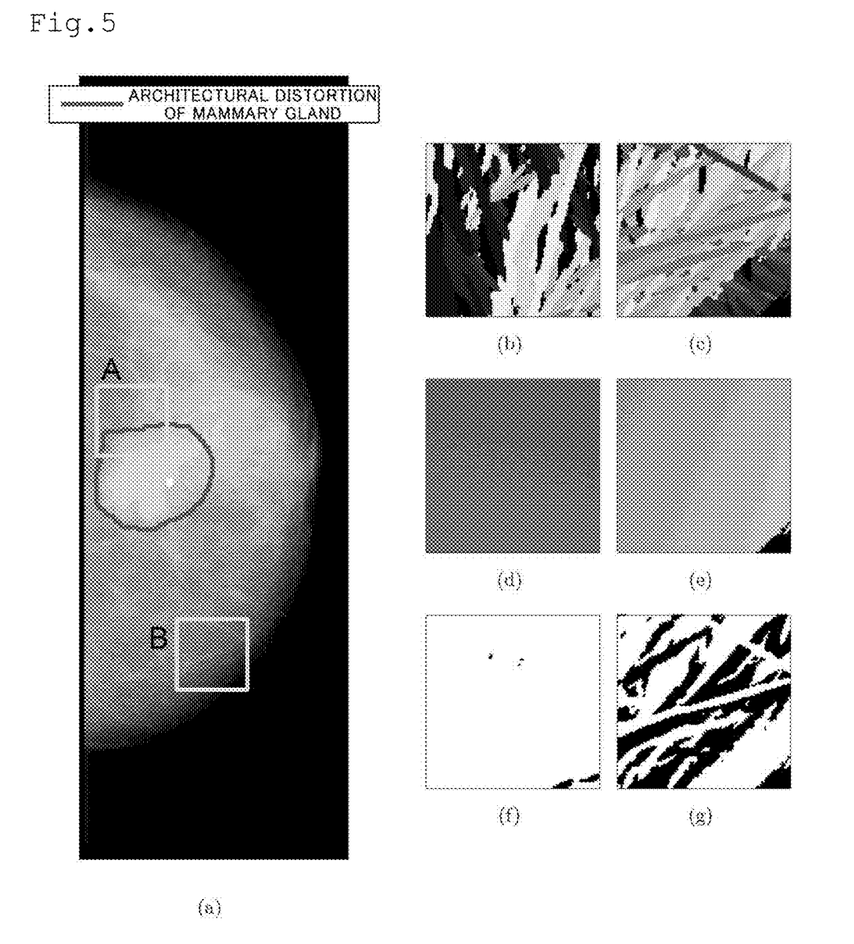
FIG. 5(a) illustrates an X-ray image of the breast received by the breast cancer detection system illustrated in FIG. 1.
FIG. 5(b) illustrates an image illustrating an orientation Θ of linear components of region A in FIG. 5(a)
FIG. 5(c) illustrates an image illustrating an orientation Θ of linear components of region B in FIG. 5(a)
FIG. 5(d) illustrates an image illustrating an orientation Φ of the mammary gland in a normal architecture model of region A in FIG. 5(a)
FIG. 5(e) illustrates an image illustrating an orientation Φ of the mammary gland in a normal architecture model of region B in FIG. 5(a)
FIG. 5(f) illustrates an image illustrating h(x,y) of region A in FIG. 5(a)
FIG. 5(g) illustrates an image illustrating h(x,y) of region B in FIG. 5(a).

Next, the flow of processes of the breast cancer detection system according to the embodiment of the present invention will be described with reference to FIG. 3 to FIGS. 5(a) to 5(g). As illustrated in FIG. 3, first, the receiving means 11 receives X-ray images of the breast captured by a mammographic X-ray imaging device (step 31), and the preprocessing means 21 of the main controller 13 extracts architectural distortion candidates of the mammary gland. FIG. 4(a) illustrates an example of the X-ray image of the breast. In the preprocessing means 21, first, the breast region extracting means 25 removes the pectoral region from the X-ray image of the breast to extract the breast region (step 32), and the DoG filtering means 26 performs DoG filtering to detect a local contrast (step 33). Subsequently, the threshold processing means 27 performs threshold processing on the image obtained after the DoG filtering to extract the architectural distortion candidates of the mammary gland (step 34).

After the processing of the preprocessing means 21 ends, the model calculating means 22 calculates a normal architecture model of the mammary gland that scatters in a fan shape from the nipple toward the greater pectoral muscle with respect to the received X-ray image of the breast to calculate the orientation Φ(x,y) of the mammary gland (step 35). Moreover, the orientation extracting means 23 extracts the orientation Θ(x,y) of the linear components of an image texture of a region that form the shape of the shadows in the received X-ray image of the breast using Gabor filters (step 36). FIGS. 4(b) and 4(c) illustrate an image illustrating the orientation Φ(x,y) of the mammary gland in the normal architecture model calculated for the X-ray image of the breast of FIG. 4(a) and an image illustrating the extracted orientation Θ(x,y) of the linear components. In FIG. 4(c), m in Equation (10) is 12.

Subsequently, the lesion determining means 24 calculates a feature quantity R using Equation (1) from the orientation Φ(x,y) of the mammary gland in the normal architecture model calculated by the model calculating means 22 and the orientation Θ(x,y) extracted by the orientation extracting means 23 with respect to the region of interest in the X-ray image of the breast including the architectural distortion candidates of the mammary gland detected by the preprocessing means 21 (step 37). Further, the lesion determining means 24 determines whether the architectural distortion candidates are architectural distortions of the mammary gland based on the feature quantity R (step 38).

FIGS. 5(a) to 5(g) illustrate examples of the feature quantity R calculated for a region (region A in FIG. 5(a)) including architectural distortions of the X-ray image of the breast of FIG. 4(a) and a region (region B in FIG. 5(a)) of the normal mammary gland architecture. FIG. 5(f) illustrates h(x,y) of Equation (1), calculated from the orientation Θ(x,y) illustrated in FIG. 5(b) and the orientation Φ(x,y) of the mammary gland in the normal architecture model illustrated in FIG. 5(d) with respect to region A including architectural distortions. The feature quantity R calculated from h(x,y) was 0.99. Moreover, FIG. 5(g) illustrates h(x,y) of Equation (1), calculated from the orientation Θ(x,y) illustrated in FIG. 5(c) and the orientation Φ(x,y) of the mammary gland in the normal architecture model illustrated in FIG. 5(e) with respect to region B of the normal mammary gland architecture. The feature quantity R calculated from h(x,y) was 0.59. When a value such as 0.8, for example is set as the threshold of the feature quantity R, it is possible to accurately determine architectural distortions of the mammary gland illustrated in FIGS. 5(a) to 5(g).

The breast cancer detection system according to the embodiment of the present invention calculates a normal architecture model of the mammary gland, calculates a feature quantity of architectural distortion candidates in the X-ray image of the breast based on the normal architecture model, and determines whether the architectural distortion candidates are architectural distortions based on the feature quantity. Thus, it is possible to accurately quantify the features of lesions by taking the positions of architectural distortion candidates on the breast region into consideration and to make determination. When the feature quantity is the difference between the orientation of the mammary gland in the normal architecture model and the orientation of the linear components that form the shape of the shadows in the X-ray image of the breast, the feature quantity can be easily calculated by a difference calculation. Thus, the feature quantity of architectural distortions such as speculations wherein the mammary gland scatters in a radial form from one point can be quantified with high accuracy. In this manner, the breast cancer detection system according to the embodiment of the present invention can reduce a false-positive fraction and accurately detect architectural distortions of the mammary gland as compared to a case where the normal mammary gland architecture is not taken into consideration.

By using R in Equation (1) as the feature quantity, it is possible to accurately identify the features of architectural distortions. By adjusting the value of the parameter $N_m$ in Equation (1) according to the size, the contrast, and the like of noise in the X-ray image of the breast, it is possible to secure optimal detection performance. Moreover, it is possible to adjust a true-positive fraction and a false-positive fraction according to the value of the threshold of the feature quantity R used when determining architectural distortions.

In the breast cancer detection system according to the embodiment of the present invention, although the CAD system disclosed in Non-Patent Literature 3 is used as the preprocessing means 21, other conventional CAD systems disclosed in Patent Literature 2, Non-Patent Literature 1, or Non-Patent Literature 2 may be used. Moreover, the normal architecture model of the mammary gland used in the breast cancer detection system according to the embodiment of the present invention is not limited to the model which uses an exponential curve but may be an optional model as long as the mammary gland scatters in a fan shape from the nipple toward the greater pectoral muscle.

The breast cancer detection program according to the embodiment of the present invention is provided in a form of being recorded on a computer-readable recording medium such as CD (CD-ROM, CD-R, CD-RW, and the like), and DVD (DVD-ROM, DVD-RAM, DVD-R, DVD-RW, DVD+R, DVD+RW, and the like), for example. In this case, a computer can read the breast cancer detection program from the recording medium, transmit and store the program to and in an internal or external storage means of the computer, and use the program. Moreover, the breast cancer detection program according to the embodiment of the present invention may be recorded on a storage means (recording medium) such as a magnetic disk, an optical disc, or an magneto-optical disc and be provided from the storage means to a computer via a communication line.

Here, the computer is a concept that includes hardware and an operating system (OS) and means hardware operating under the control of the OS. Moreover, when an OS is not required and hardware is operated by an application program only, the hardware itself corresponds to the computer. Hardware includes at least a microprocessor such as a CPU and means for reading a computer program recorded on a recording medium.

An application program as the breast cancer detection program according to the embodiment of the present invention includes program codes for causing a computer to realize the above-described functions. Moreover, some of the functions may be realized by an OS rather than the application program. Various compute-readable media such as an internal storage means (memory such as RAM or ROM), an external storage means, and the like of the computer or a print on which symbols such as barcodes are printed may be used as the computer-readable recording medium according to the embodiment of the present invention in addition to the flexible disk, CD, DVD, magnetic disk, optical disc, and magneto-optical disc.

PRACTICAL EXAMPLE 1

The breast cancer detection system according to the embodiment of the present invention was applied to clinical data and the architectural distortion detection performance was examined. DDSM (digital database for screening mammography) which is a worldwide standard database was used as performance evaluation data, and 100 X-ray images of the breast including 50 cases including architectural distortions and 50 normal case examples were selected from the DDSM and were used. The spatial resolution of these images was 0.05 mm/pixel and the density resolution thereof was 12 bits.

FROC (free-response receiver operating characteristic) curves were used in evaluation of the detection performance. The FROC curve is a graph of which the horizontal axis represents the number of false positives per image (FPI) and the vertical axis represents true-positive fraction (TPF). The FROC curve is frequently used for performance evaluation when a plurality of false positives occur as in mammography CAD. In the FROC curve, it is determined that the corner is closer to the top-left corner of the graph, the higher the detection performance of the curve is.

$K=1.6$, $\sigma=37.5, 50, 62.5, 75$, and $87.5$ were used as the parameters of the DoG filtering. $\lambda=4$, $\gamma=1/256$, $\sigma=\lambda/\{2(2 \ln 2)^{1/2}\}$, and $m=12$ were used as the parameters of the Gabor filter, the line width was set to 0.8 mm, and the length was set to 12.8 mm.

Figure 6:
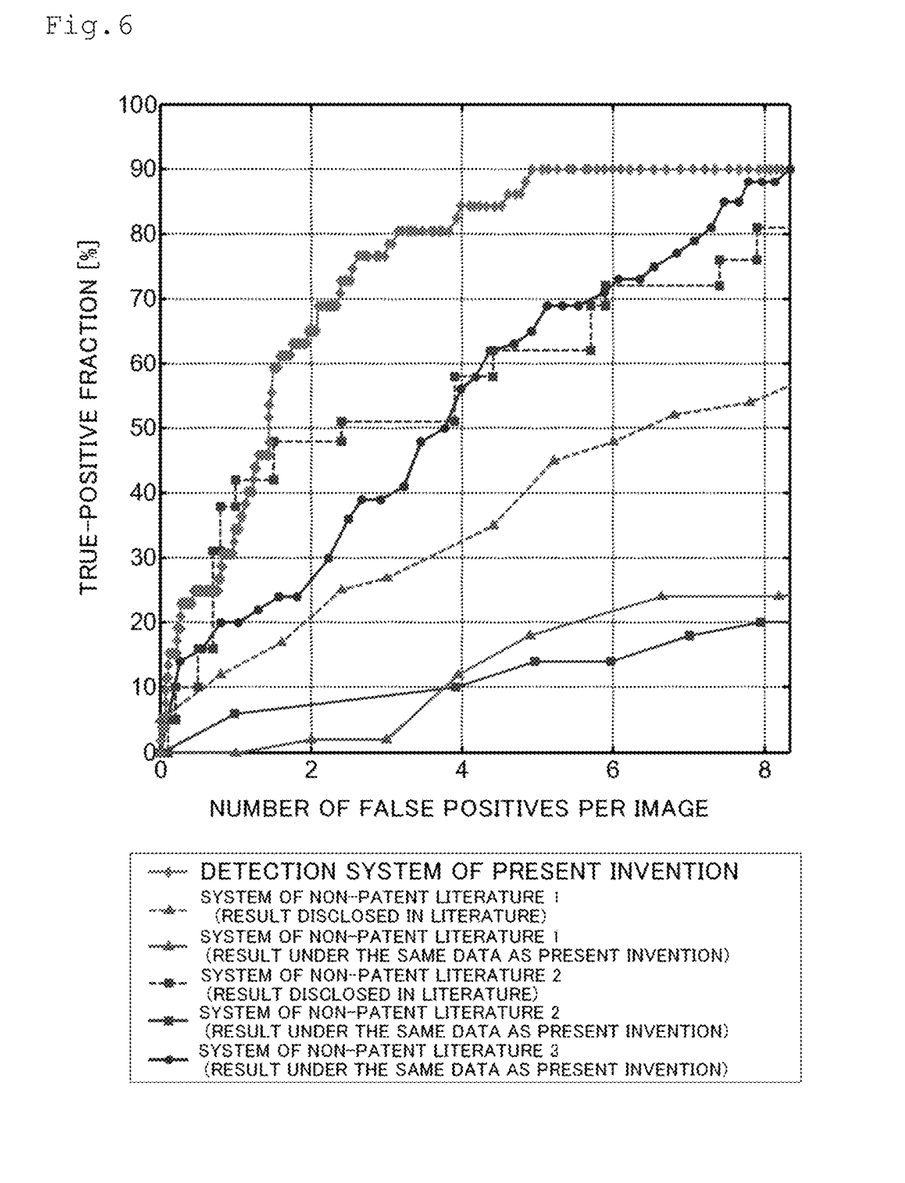
FIG. 6 is a graph illustrating FROC curves obtained by the breast cancer detection system illustrated in FIG. 1.

The calculated FROC curve is illustrated in FIG. 6. Moreover, comparison FROC curves calculated by the CAD systems of Non-Patent Literatures 1 to 3 are also illustrated in FIG. 6. The result obtained by Non-Patent Literature 3 is the result obtained by the preprocessing means 21 of the breast cancer detection system according to the embodiment of the present invention, and the same parameters as those of the breast cancer detection system according to the embodiment of the present invention are used as the parameters of the DoG filtering.

As illustrated in FIG. 6, it was confirmed that the FROC curve of the breast cancer detection system according to the embodiment of the present invention was positioned closer to the top-left corner than the curves of the other methods and had a performance superior to that of the conventional systems. Moreover, in the CAD system of Non-Patent Literature 3, the number of false positives per image was 7.2 at a true-positive fraction of 80%. In the breast cancer detection system according to the embodiment of the present invention, since the normal architecture model of the mammary gland was introduced and the feature quantity R was used, the number of false positives per image was improved remarkably to 3.1 at the true-positive fraction of 80%. Therefore, it can be said that the breast cancer detection system according to the embodiment of the present invention can reduce the false-positive fraction remarkably while maintaining the true-positive fraction and improve the overall performance.

REFERENCE SIGNS LIST

11: Receiving means
12: Storage means
13: Main controller
21: Preprocessing means
25: Breast region extracting means
26: DoG filtering means
27: Threshold processing means
22: Model calculating means
23: Orientation extracting means
24: Lesion determining means
14: Output means

The invention claimed is:

1. A breast cancer detection system for detecting an architectural distortion of the mammary gland included in an X-ray image of the breast, the breast cancer detection system comprising:
   a processor programmed to:
       calculate a normal architecture model of the mammary gland that scatters in a fan shape from the nipple toward the greater pectoral muscle with respect to the X-ray image of the breast;
       extract orientations of linear components of an image texture of a region that form a shape of a shadow in the X-ray image of the breast; and compare the orientation of the mammary gland in the calculated normal architecture model and the extracted orientation with respect to a region of interest in the X-ray image of the breast including architectural distortion candidates of the mammary gland detected by preprocessing to: (i) calculate a feature quantity based on a difference between the orientations, and (ii) determine whether the candidates are an architectural distortion of the mammary gland based on the feature quantity.

2. The breast cancer detection system according to claim 1, wherein
the processor calculates the feature quantity R according to the following equation in which, for a plurality of coordinates (x,y) in the region of interest, $\Phi(x,y)$ is the orientation of the mammary gland in the calculated normal architecture model, $\Theta(x,y)$ is the extracted orientation, $N_m$ is a parameter for determining an allowable range of matching orientations, and $N_{ROI}$ is the number of coordinates

[Equation 1]

$$R = \frac{\sum_x \sum_y h(x,y)}{N_{ROI}}$$

where $$h(x,y) = \begin{cases} 0, & |\Phi(x,y) - \Theta(x,y)| \leq \frac{\pi}{N_m} \\ 1, & \text{otherwise} \end{cases}.$$

3. The breast cancer detection system according to claim 2, wherein
the processor extracts orientations of linear components of an image texture of a region in the X-ray image of the breast using a Gabor filter.

4. The breast cancer detection system according to claim 3, wherein
the processor calculates the normal architecture model of the mammary gland using an exponential curve.

5. The breast cancer detection system according to claim 2, wherein
the processor calculates the normal architecture model of the mammary gland using an exponential curve.

6. The breast cancer detection system according to claim 1, wherein
the processor extracts orientations of linear components of an image texture of a region in the X-ray image of the breast using a Gabor filter.

7. The breast cancer detection system according to claim 6, wherein
the processor calculates the normal architecture model of the mammary gland using an exponential curve.

8. The breast cancer detection system according to claim 1, wherein
the processor calculates the normal architecture model of the mammary gland using an exponential curve.

9. A breast cancer detection method for detecting an architectural distortion of the mammary gland included in an X-ray image of the breast, comprising:
a model calculating step of calculating, by a computer, a normal architecture model of the mammary gland that scatters in a fan shape from the nipple toward the greater pectoral muscle with respect to the X-ray image of the breast;
an orientation extracting step of extracting, by the computer, an orientation of linear components of an image texture of a region that form a shape of a shadow in the X-ray image of the breast; and
a lesion determining step of comparing, by the computer, the orientation of the mammary gland in the normal architecture model calculated by the model calculating step and the orientation extracted by the orientation extracting step with respect to a region of interest in the X-ray image of the breast including architectural distortion candidates of the mammary gland detected by preprocessing to: (i) calculate a feature quantity based on a difference between the orientations, and (ii) determine whether the candidates are an architectural distortion of the mammary gland based on the feature quantity.

10. The breast cancer detection method according to claim 9, wherein
the lesion determining step calculates the feature quantity R according to the following equation in which, for a plurality of coordinates (x,y) in the region of interest, $\Phi(x,y)$ is the orientation of the mammary gland in the normal architecture model calculated by the model calculating step, $\Theta(x,y)$ is the orientation extracted by the orientation extracting step, $N_m$ is a parameter for determining an allowable range of matching orientations, and $N_{ROI}$ is the number of coordinates

[Equation 2]

$$R = \frac{\sum_x \sum_y h(x,y)}{N_{ROI}}$$

where $$h(x,y) = \begin{cases} 0, & |\Phi(x,y) - \Theta(x,y)| \leq \frac{\pi}{N_m} \\ 1, & \text{otherwise} \end{cases}.$$

11. The breast cancer detection method according to claim 10, wherein
the orientation extracting step extracts orientations of linear components of an image texture of a region in the X-ray image of the breast using a Gabor filter.

12. The breast cancer detection method according to claim 11, wherein
the model calculating step calculates the normal architecture model of the mammary gland using an exponential curve.

13. The breast cancer detection method according to claim 10, wherein
the model calculating step calculates the normal architecture model of the mammary gland using an exponential curve.

14. The breast cancer detection method according to claim 9, wherein
the orientation extracting step extracts orientations of linear components of an image texture of a region in the X-ray image of the breast using a Gabor filter.

15. The breast cancer detection method according to claim 14, wherein
the model calculating step calculates the normal architecture model of the mammary gland using an exponential curve.

16. The breast cancer detection method according to claim 9, wherein
the model calculating step calculates the normal architecture model of the mammary gland using an exponential curve.

17. A non-transitory computer-readable medium storing a breast cancer detection program thereon, for detecting an architectural distortion of the mammary gland included in an X-ray image of the breast, the program causing a computer to perform steps comprising:
  a model calculating step that calculates a normal architecture model of the mammary gland that scatters in a fan shape from the nipple toward the greater pectoral muscle with respect to the X-ray image of the breast;
  an orientation extracting step that extracts orientations of linear components of an image texture of a region that form a shape of a shadow in the X-ray image of the breast; and
  a lesion determining step that compares the orientation of the mammary gland in the normal architecture model calculated by the model calculating step and the orientation extracted by the orientation extracting step with respect to a region of interest in the X-ray image of the breast including architectural distortion candidates of the mammary gland detected by preprocessing to: (i) calculate a feature quantity based on a difference between the orientations, and (ii) determine whether the candidates are an architectural distortion of the mammary gland based on the feature quantity.

* * * * *